(12) United States Patent
Portmann et al.

(10) Patent No.: US 6,455,556 B2
(45) Date of Patent: Sep. 24, 2002

(54) CRYSTAL MODIFICATIONS OF 1-(2,6-DIFLUOROBENZYL)-1H-1,2,3-TRIAZOLE-4-CARBOXAMIDE

(75) Inventors: Robert Portmann, Pratteln; Urs Christoph Hofmeier, St. Pantaleon; Andreas Burkhard, Basel; Walter Scherrer, Rheinfelden; Martin Szelagiewicz, Münchenstein, all of (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/871,366

(22) Filed: May 31, 2001

Related U.S. Application Data

(63) Continuation of application No. 09/599,688, filed on Jun. 22, 2000, now abandoned, which is a continuation of application No. 09/125,330, filed as application No. PCT/EP98/03428 on Jun. 8, 1998, now abandoned.

(30) Foreign Application Priority Data

Jun. 10, 1997 (CH) ................................................ 1404/97

(51) Int. Cl.⁷ .................... A61K 31/4192; C07D 249/04
(52) U.S. Cl. ........................................ 514/359; 548/255
(58) Field of Search ........................... 514/359; 548/255

(56) References Cited

U.S. PATENT DOCUMENTS 4,789,680 A    12/1988   Meier, II ..................... 514/359

FOREIGN PATENT DOCUMENTS

EP    0 199 262 A    10/1986

OTHER PUBLICATIONS

Munzel K., I Progress in Drug Research, vol. 10, pp. 277–30 (1996).

Munzel K., II Progress in Drug Research, vol. 14, pp. 309–21 (1970).

*Primary Examiner*—Patricia L. Morris
(74) *Attorney, Agent, or Firm*—Joseph J. Borovian

(57) ABSTRACT

The invention relates to the novel modifications B and C of the compound 1-(2,6-difluorobenzyl)-1H-1,2,3-triazole-4-carboxamide of the formula

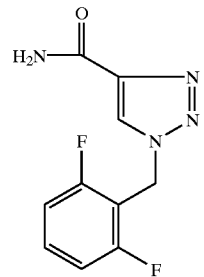

their use and pharmaceutical preparations comprising this crystal modifications.

18 Claims, 2 Drawing Sheets

CRYSTAL MODIFICATIONS OF 1-(2,6-DIFLUOROBENZYL)-1H-1,2,3-TRIAZOLE-4-CARBOXAMIDE

This is a continuation of application No. 09/599,688 filed Jun. 22, 2000, now abandoned, which is a continuation of application No. 09/125,330, having a 371 date of Sep. 8, 1998, now abandoned, which application is 371 of international application No. PCT/EP98/03428 filed Jun. 8, 1998.

BACKGROUND OF THE INVENTION

The compound 1-(2,6-difluorobenzyl)-1H-1,2,3-triazole-4-carboxamide of the formula

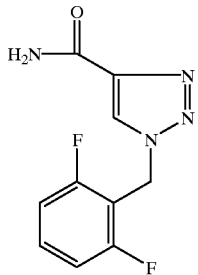

is described in the European Patent Application with the Publication No. 0 199 262 A2 (EP 199262), for example in Example 4. Valuable pharmacological properties are attributed to this compound; thus, it can be used, for example, as an antiepileptic. The compound 1-(2,6-difluorobenzyl)-1H-1,2,3-triazole-4-carboxamide is obtained according to EP 199262, starting from 2,6-difluorobenzyl azide via the formation of 1-(2,6-difluorobenzyl)-1H-1,2,3-triazole-4-carboxylic acid, the procedure being analogous to Example 2.

EP 199262 provides no information at all about possible crystal modifications obtained. If the method according to Example 4 is used in conjunction with Example 2, the crude 1-(2,6-difluorobenzyl)-1H-1,2,3-triazole-4-carboxamide product obtained is finally crystallized from ethanol. However, EP 199262 gives no indication that such recrystallization is specifically to be applied, or on particular conditions that might be adopted. It has now surprisingly been found that the different crystal modifications (polymorphism) characterized below can be prepared by choice of specially selected process conditions, for example through the choice of an appropriate solvent for the recrystallization or the duration of the recrystallization.

DESCRIPTION OF THE INVENTION 1-(2,6-Difluorobenzyl)-1H-1,2,3-triazole4-carboxamide can be obtained in the novel crystal modifications A, A', B and C. These crystal modifications differ with respect to their thermodynamic stability, in their physical parameters, such as the absorption pattern of IR and Raman spectra, in X-ray structure investigations and in their preparation processes.

The invention relates to the novel crystal modifications B and C, their preparation and use in pharmaceutical preparations comprising the crystal modifications.

The modification A', compared with A, has defects in the crystal lattice. These are detectable, for example, by X-ray analysis, e.g. by smaller line spacings with otherwise predominantly identical lines or bands.

The crystal modification A of 1-(2,6-difluorobenzyl)-1H-1,2,3-triazole4-carboxamide melts at 242° C. (239-245° C.).

In the FT infrared (FT-IR) spectrum (KBr pellet - transmission method), modification A or A' differs from modifications B and C predominantly in the shape and in the relative intensity of many bands. Particularly characteristic are the bands at 3412 cm$^{-1}$ and 3092 cm$^{-1}$ [cf. FIG. 1], which are not present in the FT-IR spectra of the modifications B and C. In the range 4000–600 cm$^{-1}$, inter alia the following bands are obtained for modification A: 3412, 3189, 3092, 1634, 1560, 1473, 1397, 1325, 1300, 1284, 1235, 1125, 1053, 1036, 1014, 885, 840, 799, 781, 723, 688 and 640 cm$^{-1}$. For example, the apparatus IFS 88 (Bruker) can be used for recording of each of the FT-IR spectra.

In the FT Raman spectrum (powder—reflection method 180°), the modification A or A' differs from modifications B and C predominantly in the shape and in the relative intensity of many bands. Particularly characteristic are the band at 1080 cm$^{-1}$ [cf. FIG. 2], which is not present in the Raman spectra of the modifications B and C. In the range 3400–300 cm$^{-1}$, inter alia the following bands are obtained for the modification A: 3093, 2972, 1628, 1614, 1558, 1465, 1446, 1393, 1279, 1245, 1147, 1080, 1061, 1036, 1014, 840, 724, 691, 667, 550, 499, 437 and 368 cm$^{-1}$. For example, the apparatus RFS 100 (Bruker) can be used for recording of each of the FT Raman spectra.

The modification A has an X-ray powder pattern with characteristic lines with interplanar spacings (d values) of 10.5 Å, 5.14 Å, 4.84 Å, 4.55 Å, 4.34 Å, 4.07 Å, 3.51 Å, 3.48 Å, 3.25 Å, 3.19 Å, 3.15 Å, 3.07 Å, 2.81 Å [cf. Table 1]. The measurement can be carried out, for example, in transmission geometry on an FR 552 Guinier camera from Enraf-Nonius, Delft (The Netherlands), using copper K$\alpha_1$ radiation (wavelength $\lambda$=1.54060 Å). The patterns recorded on X-ray film were measured using an LS-18 line scanner from Johannsson, Täby (Sweden) and evaluated using the Scanpi software (P. E. Werner, University of Stockholm).

Characteristic for the modification A is the thermogram in differential scanning calorimetry. It has an endothermic peak in the range from 230° C. to 260° C. The peak temperature is 239-245° C., and the endothermic signal is 209 J/g±10 J/g. The measurement was carried out on a Perkin Elmer DSC 7 in a closed pan with a heating rate of 20 K/minute. The typical sample quantity is about 4 mg. As a typical distinguishing feature compared with the modifications B and C, the thermogram of the modification A has no further thermal signal.

Crystals of the modification A' have the same crystal structure as modification A. They differ from the modification A in the X-ray powder pattern in that they have slightly smaller line spacings between specific pairs of lines. These are the pairs of lines with the following interplanar spacings: 3.68 Å and 3.64 Å, 3.51 Å and 3.48 Å, 3.19 Å and 3.15 Å.

In the FT-IR spectrum (KBr pellet—transmission method), the novel modification B differs from the modification A or A' and C predominantly in the shape and in the relative intensity of many bands. Particularly characteristic is a band at 1678 cm$^{-1}$ [cf. FIG. 1], which is not to be observed in the corresponding spectra of the modifications A and C. In the range 4000–600 cm$^{-1}$, inter alia the following bands are obtained for the modification B: 3404, 3199, 3125, 1678, 1635, 1560, 1475, 1393, 1357, 1322, 1286, 1237, 1051, 1036, 1028, 889, 837, 800, 719, 667 and 645 cm$^{-1}$. For example, the apparatus IFS 85 (Bruker) can be used for recording of each of the FT-IR spectra.

In the FT Raman spectrum (powder—reflection method 180°), the novel modification B differs from the modifications A or A' and C predominantly in the shape and in the relative intensity of many bands. Particularly characteristic are the bands at 3166 cm$^{-1}$ and 1086 cm$^{-1}$ [cf. FIG. 2], which are not present in the Raman spectra of the modifications A and C. In the range 3400–300 cm$^{-1}$, inter alia the following bands are obtained for the modification B: 3166, 3089, 2970, 1678, 1628, 1614, 1559, 1464, 1441, 1391, 1275, 1244, 1147, 1086, 1062, 1036, 1014, 839, 773, 724, 690, 668, 595, 549, 500, 493, 430 and 365 cm$^{-1}$. For example, the apparatus RFS 100 (Bruker) can be used for recording of each of the FT Raman spectra.

The novel modification B has an X-ray powder pattern with characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å, 2.83 Å [cf. Table 1].

In the thermogram in differential scanning calorimetry, the novel modification B has, in addition to an endothermic signal in the range from 230° C. to 260° C. (peak temperature 239–245° C.), a weak thermal signal at 205° C. (180°–220° C.) as a typical distinguishing feature compared with the modifications A or A' and C.

In the FT-IR spectrum (KBr pellet—transmission method), the novel modification C differs from the modifications A or A' and B predominantly in the shape and in the relative intensity of many bands. Particularly characteristic is a band at 3137 cm$^{-1}$ [cf. FIG. 1], which is not to be observed in the corresponding spectra of the modifications A and B.

In the range 4000–600 cm$^{-1}$, inter alia the following bands are obtained for the novel modification C: 3396, 3287, 3137, 1657, 1631, 1602, 1559, 1475, 1392, 1323, 1287, 1237, 1122, 1104, 1047, 1035, 1012, 876, 839, 797, 773, 729 and 653 cm$^{-1}$. For example, the apparatus IFS 85 (Bruker) can be used for recording of each of the FT-IR spectra.

In the FT Raman spectrum (powder—reflection method 180°), the modification C differs from the modifications A or A' and B predominantly in the shape and in the relative intensity of many bands. Particularly characteristic are the bands at 3137 cm$^{-1}$ and 1602 cm$^{-1}$ [cf. FIG. 2], which are not present in the Raman spectra of the modifications A and B. In the range 3400–300 cm$^{-1}$, inter alia the following bands are obtained for the modification C: 3137, 3080, 3012, 2971, 1673, 1629, 1602, 1561, 1436, 1271, 1248, 1105, 1065, 1035, 1013, 839, 800, 767, 726, 690, 672, 593, 549, 500, 492, 435 and 370 cm$^{-1}$. For example, the apparatus RFS 100 (Bruker) can be used for recording of each of the FT Raman spectra.

The novel modification C has an X-ray powder pattern with characteristic lines with interplanar spacings (d values) of 9.0 Å, 4.73 Å, 4.65 Å, 3.75 Å, 3.54 Å, 3.42 Å, 3.25 Å [cf. Table 1]. In the thermogram in differential scanning calorimetry, the modification C has, in addition to an endothermic signal in the range of 230° C. to 260° C. (peak temperature 239–245° C.), a very broad, weak, exothermic signal in the region of 180° C. compared with the modifications A or A' and B.

TABLE 1

Characterization of the modifications A, B and C (X-ray powder patterns):

| Modification A: | | Modification B: | | Modification C: | |
|---|---|---|---|---|---|
| d [Å] | Intensity | d [Å] | Intensity | d [Å] | Intensity |
| 10.9 | weak | 11.0 | medium | 9.0 | medium |
| 10.5 | medium | 8.3 | medium | 7.0 | weak |
| 6.6 | weak | 8.1 | very weak | 5.49 | weak |
| 5.63 | weak | 5.68 | very weak | 5.11 | very weak |
| 5.25 | weak | 5.18 | very strong | 4.80 | weak |
| 5.14 | medium | 5.11 | weak | 4.73 | strong |
| 4.94 | weak | 4.88 | medium | 4.65 | very strong |
| 4.84 | very strong | 4.80 | strong | 4.47 | very weak |
| 4.55 | strong | 4.71 | very weak | 4.19 | very weak |
| 4.42 | very weak | 4.61 | weak | 4.11 | very weak |
| 4.34 | medium | 4.45 | weak | 3.98 | very weak |
| 4.23 | very weak | 4.42 | strong | 3.83 | very weak |
| 4.16 | weak | 4.33 | very strong | 3.75 | strong |
| 4.07 | medium | 4.19 | medium | 3.73 | weak |
| 4.01 | weak | 4.12 | strong | 3.54 | medium |
| 3.68 | very weak | 4.09 | weak | 3.50 | weak |
| 3.64 | very weak | 3.99 | very weak | 3.42 | strong |
| 3.60 | weak | 3.95 | very weak | 3.25 | medium |
| 3.56 | weak | 3.84 | weak | 2.88 | very weak |
| 3.51 | medium | 3.81 | medium | 2.80 | very weak |
| 3.48 | medium | 3.65 | weak | 2.74 | very weak |
| 3.38 | very weak | 3.61 | very weak | 2.67 | very weak |
| 3.25 | strong | 3.58 | very weak | 2.64 | weak |
| 3.19 | medium | 3.54 | weak | | |
| 3.15 | medium | 3.50 | medium | | |
| 3.11 | weak | 3.47 | very weak | | |
| 3.07 | medium | 3.41 | medium | | |
| 2.93 | very weak | 3.36 | very strong | | |
| 2.87 | very weak | 3.32 | strong | | |
| 2.81 | medium | 3.28 | medium | | |
| 2.76 | weak | 3.24 | medium | | |
| 2.73 | very weak | 3.10 | weak | | |
| 2.68 | weak | 3.07 | weak | | |
| 2.62 | very weak | 3.05 | medium | | |
| 2.53 | weak | 2.93 | weak | | |
| 2.43 | weak | 2.88 | weak | | |
| 2.40 | very weak | 2.87 | very weak | | |
| | | 2.83 | medium | | |
| | | 2.66 | weak | | |
| | | 2.63 | very weak | | |
| | | 2.55 | weak | | |
| | | 2.50 | weak | | |
| | | 2.46 | weak | | |
| | | 2.44 | weak | | |
| | | 2.37 | weak | | |
| | | 2.35 | weak | | |

Single crystal X-ray analysis:

Crystal quality and unit cell of modifications A, B, and C were verified by Weissenberg and precession photographs. The intensities were measured on a four-axis Nonius CAD-4 diffractometer. The structures were solved with the SHELXS-97 and refined with the SHELXL-97 software.

Modification A

Space group: Pna2$_1$ - orthorhombic

Cell dimensions:

a = 24.756 (5)Å    b = 23.069 (4)Å    c = 5.386 (1)Å
v = 3075.9 Å$^3$    Z = 12    D$_x$ = 1.543 gcm$^{-3}$
v per formula:    V$_z$ = 256.3 Å$^3$ 9011 unique reflections; 2479 thereof significant with I>2 σ (I). 557 parameters refined. Position of all H atoms found by difference Fourier maps and refined isotropically. Reliability index R$_1$: 3.65% (wR$_2$ for all 9011 reflections: 11.34%).

Modification B
Space group: P$^{-1}$-triclinic
Cell dimensions:

| | | |
|---|---|---|
| a = 5.326(1) Å | b = 11.976(2) Å | c = 17.355(3) Å |
| α = 107.22(3)° | β = 92.17(3)° | γ = 102.11(3)° |
| v = 1027.9 Å$^3$ | Z = 4 | D$_x$ = 1.539 gcm$^{-3}$ |
| v per formula | V$_z$ = 257.0 Å$^3$ | |

4934 unique reflections; 834 thereof significant with I>2 σ (I). 232 parameters refined.

Position of all H atoms found by difference Fourier maps and refined isotropically. Reliability index R$_1$: 4.20% (wR$_2$ for all 4934 reflections: 7.93%).

Modification C
Space group: P2$_1$/C—monoclinic
Cell dimensions:

| | | |
|---|---|---|
| a = 10.982(2) Å | b = 5.350(1) Å | c = 17.945(3) Å |
| | β = 91.59(1)° | |
| v = 1053.9 Å$^3$ | Z = 4 | D$_x$ = 1.501 gcm$^{-3}$ |
| v per formula: | V$_z$ = 263.5 Å$^3$ | |

3073 unique reflections; 1071 thereof significant with I>2 σ (I). 187 parameters refined. Position of all H atoms found by difference Fourier maps and refined isotropically. Reliability index R$_1$: 5.02% (wR$_2$ for all 3073 reflections: 14.55%).

Modifications A, A', B and C have valuable pharmacological properties; in particular, they can be used for the treatment of epilepsy.

The modifications B and C have significant advantages compared with the modification A or A'.

Thus, it was found, for example, that modification B has a substantially faster dissolution rate in water and gastric fluid than modification A or A'. Consequently, when modification B is used therapeutically, a rapid onset of action is achieved, which is particularly advantageous, for example in an acute epilepsy attack.

The invention relates to the modification B of 1-(2,6-difluorobenzyl)-1H-1,2,3-triazole4-carboxamide, having the following absorption in the infrared spectrum (KBr pellet—transmission method): band at 1678 cm$^{-1}$.

The invention relates to the modification B of 1-(2,6-difluorobenzyl)-1H-1,2,3-triazole-4-carboxamide, having characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å and 2.83 Å, determined by means of an X-ray powder pattern.

The invention relates to the modification B of 1-(2,6-difluorobenzyl)-1H-1,2,3-triazole-4-carboxamide, having the characteristic lines with interplanar spacings (d values) as shown in Table 1.

The invention relates to the modification B of 1-(2,6-difluorobenzyl)-1H-1,2,3-triazole-4-carboxamide, having in the thermogram in differential scanning calorimetry a weak thermal signal at 205° C. (180-220° C.) in addition to an endothermic signal in the range from 230° C. to 260° C. (peak temperature 239–245° C.).

The invention furthermore relates to the crystal modification C of 1-(2,6-difluorobenzyl)-1H-1,2,3-triazole-4-carboxamide, having the following absorption in the infrared spectrum (KBr pellet—transmission method): band at 3137 cm$^{-1}$.

The invention relates to the modification C of 1-(2,6-difluorobenzyl)-1H-1,2,3-triazole-4-carboxamide, having characteristic lines with interplanar spacings (d values) of 9.0 Å, 4.73 Å, 4.65 Å, 3.75 Å, 3.54 Å, 3.42 Å, 3.25 Å, determined by means of an X-ray powder pattern.

The invention relates to modification C of 1-(2,6-difluorobenzyl)-1H-1,2,3-triazole-4-carboxamide, having the characteristic lines with interplanar spacings (d values) as shown in Table 1.

The invention relates to the modification C of 1-(2,6-difluorobenzyl)-1H-1,2,3-triazole4-carboxamide, having in the thermogram in differential scanning calorimetry a very broad weak exothermic signal in the region of 180° C., in addition to an endothermic signal in the range from 230° C.-260° C. (peak temperature 239–245° C.).

The invention relates to the essentially pure forms of the modifications B and C of 1-(2,6-difluorobenzyl)-1H-1,2,3-triazole-4-carboxamide. The term "essentially pure form" means purity of >95%, in particular >98%, primarily >99%, based on the modifications B and C.

The invention relates to pharmaceutical preparations comprising the modifications B and C of 1-(2,6-difluorobenzyl)-1H-1,2,3-triazole4-carboxamide. The invention relates in particular to corresponding pharmaceutical preparations for the treatment of epilepsy and subindications thereof. The invention relates to the use of the modifications B and C of 1(2,6-difluorobenzyl)-1H-1,2,3-triazole4-carboxamide for the preparation of pharmaceutical preparations, in particular for the treatment of epilepsy and subindications thereof.

The novel modifications B and C of 1-(2,6-difluorobenzyl)-1H-1,2,3-triazole4-carboxamide can be used, for example, in the form of pharmaceutical preparations which comprise a therapeutically effective amount of the active ingredient, if desired together with inorganic or organic, solid or liquid, pharmaceutically usable carriers, which are suitable for enteral, for example oral, or parenteral administration. Furthermore, the novel modifications B and C of 1-(2,6-difluorobenzyl)-1H-1,2,3-triazole-4-carboxamide can be used in the form of preparations which can be administered parenterally or of infusion solutions. The pharmaceutical preparations may be sterilized and/or may comprise excipients, for example preservatives, stabilizers, wetting agents and/or emulsifiers, solubilizers, salts for regulating the osmotic pressure and/or buffers. The present pharmaceutical preparations comprise from about 0.1% to 100%, in particular from about 1% to about 50%, of lyophilisates to about 100% of the active ingredient.

The invention also relates to the use of the modifications B and C of 1-(2,6-difluorobenzyl)- 1H-1,2,3-triazole4-carboxamide as a drug, preferably in the form of pharmaceutical preparations. The dosage may depend on various factors, such as method of administration, species, age and/or individual condition. The doses to be administered daily are between about 0.25 and about 10 mg/kg in the case of oral administration, and preferably between about 20 mg and about 500 mg for warm-blooded species having a body weight of about 70 kg.

The preparation of the modifications B and C is carried out, for example, as described in the embodiments below.

EXAMPLE 1

Modification B 1-(2,6-Difluorobenzyl)-1H-1,2,3-triazole-4-carboxamide (18.29 kg) is dissolved in formic acid (89.3 kg) at 58-63° C. while stirring. The solution is discharged in the course of about 30 minutes onto stirred methanol (105.5 l) at 20° C. to 0° C., after which washing with formic acid (6.1 kg) is carried out. A suspension forms. The product is isolated immediately by filtration and washed with cold methanol (150 l, about 4° C.). By drying in vacuo at about 60° C., the product is obtained as modification B in a yield of about 94%.

EXAMPLE 2

Modification C 1-(2,6-Difluorobenzyl)-1H-1,2,3-triazole-4-carboxamide (15.0 g) is dissolved in acetic acid (120 ml) at about 90° C. while stirring. The solution is cooled to 20° C. in the course of about 8 minutes, a suspension forming. The product is immediately isolated by filtration, washed with toluene (120 ml) and dried in vacuo at about 60° C. 10.1 g of the product are obtained as modification C. Yield 67.3%.

FORMULATION EXAMPLE 1

Film-coated tablets each containing, for example, 100, 200 or 400 mg of the modification B or C of 1-(2,6-difluorobenzyl)-1H-1,2,3-triazole-4-carboxamide with the following composition per dosage unit:

|  | mg | mg | mg |
|---|---|---|---|
| Core material |  |  |  |
| Active ingredient | 100.00 | 200.00 | 400.00 |
| Anhydrous, colloidal silica | 0.88 | 1.75 | 3.5 |
| Microcrystalline cellulose | 36.62 | 73.25 | 146.50 |
| Hydroxypropylmethyl-cellulose | 5.00 | 10.00 | 20.00 |
| Lactose | 20.00 | 40.00 | 80.00 |
| Magnesium stearate | 2.00 | 4.00 | 8.00 |
| Maize starch | 10.00 | 20.00 | 40.00 |
| Sodium carboxymethyl-cellulose | 5.00 | 10.00 | 20.00 |
| Sodium laurylsulfate | 0.50 | 1.00 | 2.00 |
| Film coat |  |  |  |
| Hydroxypropylmethyl-cellulose | 3.22 | 6.43 | 12.87 |
| Red iron oxide | 0.04 | 0.09 | 0.18 |
| Polyethylene glycol 8000, flakes | 0.58 | 1.16 | 2.32 |
| Talc | 2.33 | 4.66 | 9.31 |
| Titanium dioxide | 0.83 | 1.66 | 3.32 |

The active ingredient is granulated with demineralized water. Milled lactose, maize starch, Avicel PH 102, cellulose-HP-M-603 and sodium laurylsulfate are added to the above mixture and granulated with demineralized water.

The moist material is dried and milled. After the addition of the remaining ingredients, the homogeneous mixture is compressed to give tablet cores having the stated active ingredient content.

The tablet cores are coated with the film coat which is formed from the appropriate ingredients, the latter being dissolved or being suspended in water or in small amounts of ethanol with 5% of isopropanol.

Figure 1:
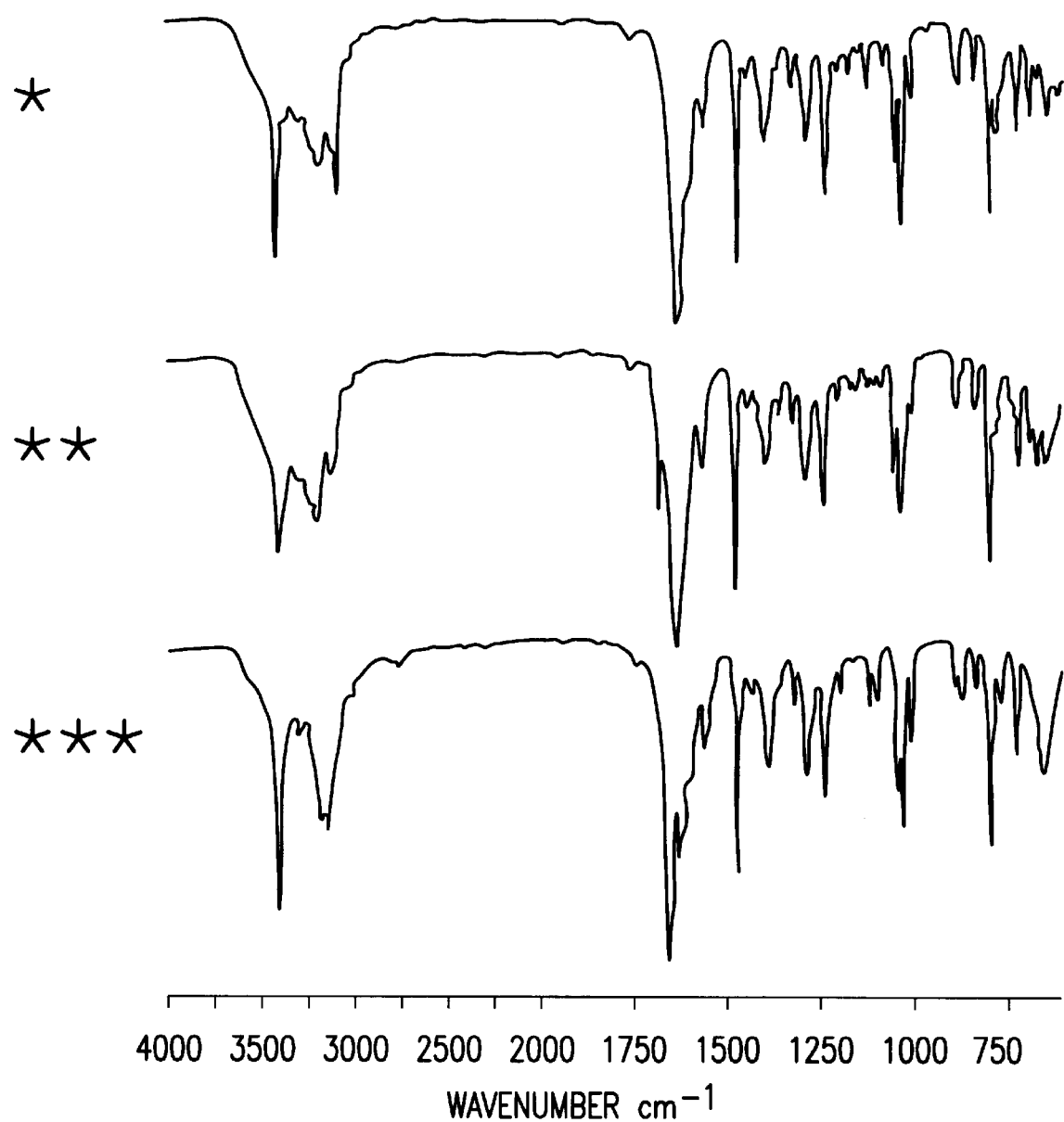
FIG. 1 shows the FT-IR spectra of the KBr pellets of crystal modifications A, B and C.
Figure 2:
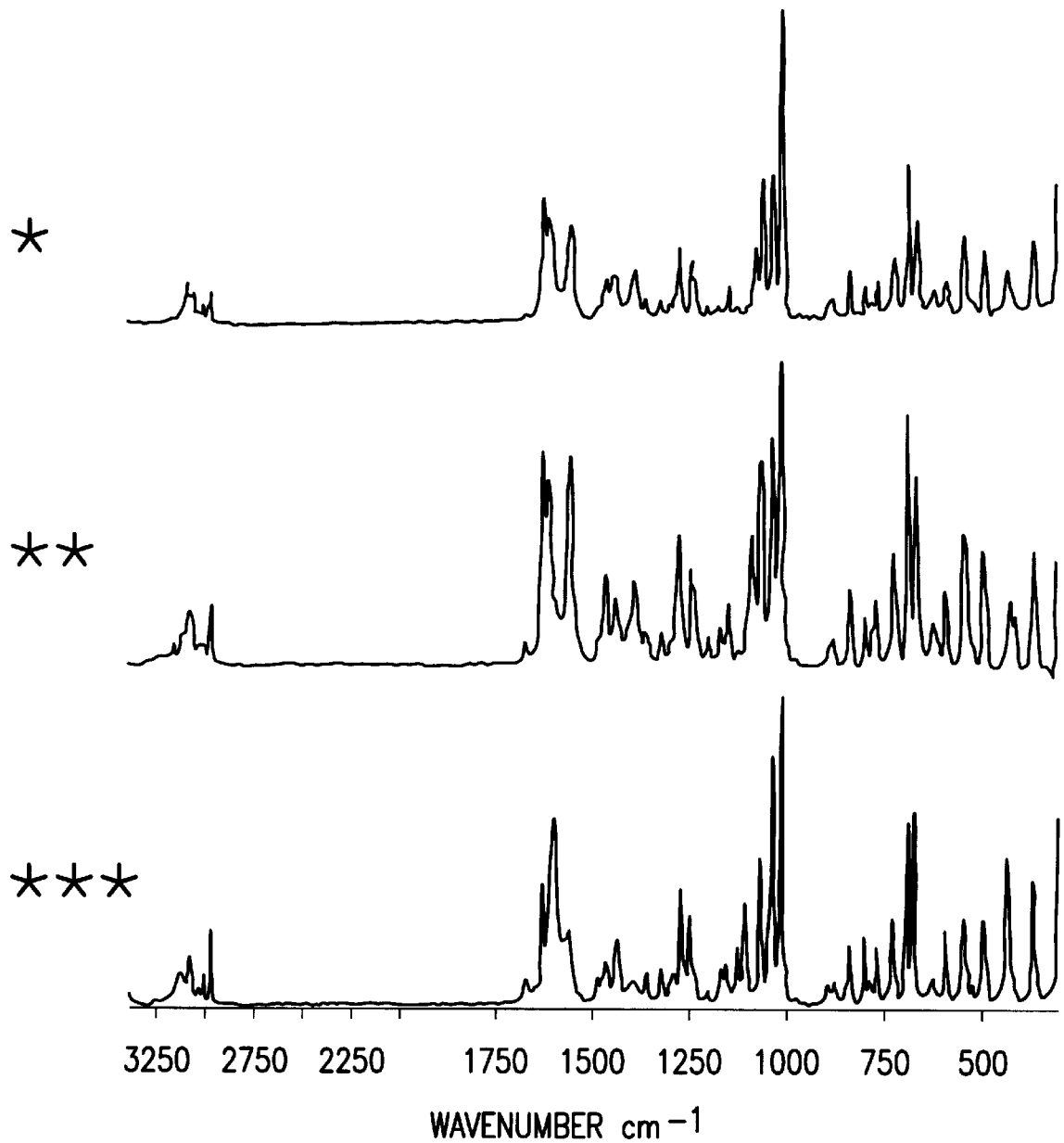
FIG. 2 shows the FT-Raman spectra of the powder of modifications A, B and C.

In both Figures, the modification A is denoted by the symbol *, the modification B by the symbol  and the modification C by the symbol *.

What is claimed is:

1. A crystal modification B of the compound 1-(2,6-difluorobenzyl)-1H-1,2,3-triazole-4-carboxamide of the formula

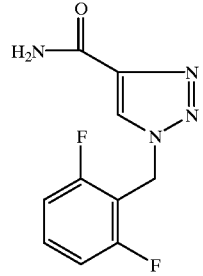

having characteristic lines with interplanar spacings (d values) of 11.0 Å, 8.3 Å, 5.18 Å, 4.88 Å, 4.80 Å, 4.42 Å, 4.33 Å, 4.19 Å, 4.12 Å, 3.81 Å, 3.50 Å, 3.41 Å, 3.36 Å, 3.32 Å, 3.28 Å, 3.24 Å, 3.05 Å and 2.83 Å, determined by means of an X-ray powder pattern.

2. A crystal modification according claim 1, which has an X-ray powder pattern having the following characteristic lines with interplanar spacings (d values) of 11.0 Å (medium), 8.3 Å (medium), 8.1 Å (very weak), 5.18 Å (very strong), 5.11 Å (weak), 4.88 Å (medium), 4.80 Å (strong), 4.71 Å (very weak), 4.61 Å (weak), 4.45 Å (weak), 4.42 Å (strong), 4.33 Å (very strong), 4.19 Å (medium), 4.12 Å (strong), 4.09 Å (weak), 3.99 Å (very weak), 3.95 Å (very weak), 3.84 Å (weak), 3.81 Å (medium), 3.65 Å (weak), 3.61 Å (very weak), 3.58 Å (very weak), 3.54 Å (weak), 3.50 Å (medium), 3.47 Å (very weak), 3.41 Å (medium), 3.36 Å (very strong), 3.32 Å (strong), 3.28 Å (medium), 3.24 Å (medium), 3.10 Å (weak), 3.07 Å (weak), 3.05 Å (medium), 2.93 Å (weak), 2.88 Å (weak), 2.87 Å (very weak), 2.83 Å (medium), 2.66 Å (weak), 2.63 Å (very weak), 2.55 Å (weak), 2.50 Å (weak), 2.46 Å (weak), 2.44 Å (weak), 2.35 Å (weak).

3. A crystal modification according to claim 1, having the following absorption in the FT-IR spectrum (KBr pellet—transmission method): 1678 $cm^{-1}$.

4. A crystal modification according to claim 3, having the following absorptions in the FT-IR spectrum (KBr pellet—transmission method): 3404, 3199, 3125, 1678, 1635, 1560, 1475, 1393, 1357, 1322, 1286, 1237, 1051, 1036, 1028, 889, 837, 800, 719, 667 and 645 $cm^{-1}$.

5. A crystal modification according to any one of claim 1, having the following absorptions in the FT-Raman spectrum (powder—reflection method 180°): 3166, 3089, 2970, 1678, 1628, 1614, 1559, 1464, 1441, 1391, 1275, 1244, 1147, 1086, 1062, 1036, 1014, 839, 773, 724, 690, 668, 595, 549, 500, 493, 430 and 365 $cm^{-1}$.

6. A crystal modification B according to any one of claim 1, having in the thermogram in differential scanning calorimetry a weak thermal signal at 205° C. (180–220° C.) in addition to an endothermic signal in the range from 230° C. to 260° C. (peak temperature 239–245° C.).

7. A crystal modification C of the compound 1-(2,6-difluorobenzyl)-1H-1,2,3-triazole4- carboxamide of the formula

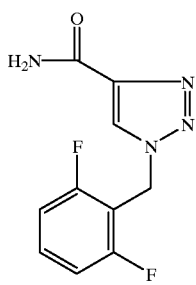

having characteristic lines with interplanar spacings (d values) of 9.0 Å, 4.73 Å, 4.65 Å, 3.75 Å, 3.54 Å, 3.42 Å, 3.25 Å, determined by means of an X-ray powder pattern.

8. A crystal modification according to claim 7, having an X-ray powder pattern with the following characteristic lines with interplanar spacings (d values) of 9.0 Å (medium), 7.0 Å (weak), 5.49 Å (weak), 5.11 Å (very weak), 4.80 Å (weak), 4.73 Å (strong), 4.65 Å (very strong), 4.47 Å (very weak), 4.19 Å (very weak), 4.11 Å (very weak), 3.98 Å (very weak), 3.83 Å (very weak), 3.75 Å (strong), 3.73 Å (weak), 3.54 Å (medium), 3.50 Å (weak), 3.42 Å (strong), 3.25 Å (medium), 2.88 Å (very weak), 2.80 Å (very weak), 2.74 Å (very weak), 2.67 Å (very weak), 2.64 Å (weak).

9. A crystal modification according to claim 7, having the following absorption in the infrared spectrum (KBr pellet—transmission method): 3137 cm$^{-1}$.

10. A crystal modification according to claim 9, having the following absorptions in the infrared spectrum (KBr pellet—transmission method): 3396, 3287, 3137, 1657, 1631, 1602, 1559, 1475, 1392, 1323, 1287, 1237, 1122, 1104, 1047, 1035, 1012, 876, 839, 797, 773, 729 and 653 cm$^{-1}$.

11. A crystal modification according to any one of claim 7, having the following absorptions in the FT-Raman spectrum (powder—reflection method 180°): 3137, 3080, 3012, 2971, 1673, 1629, 1602, 1561, 1436, 1271, 1248, 1105, 1065, 1035, 1013, 839, 800, 767, 726, 690, 672, 593, 549, 500, 492, 435 and 370 cm$^{-1}$.

12. A crystal modification C according to any one of claim 7, having in the thermogram in differential scanning calorimetry a very broad, weak, exothermic signal in the region of 180° C., in addition to an endothermic signal in the range from 230° C. to 260° C. (peak temperature 239–245° C).

13. A crystal modification B according to any one of claim 1 in essentially pure form.

14. A crystal modification C according to claim 7 in essentially pure form.

15. A pharmaceutical composition comprising a pharmaceutically acceptable carrier or diluent and a therapeutically effective amount of crystal modification B of the compound 1-(2,6- difluorobenzyl)-1H-1,2,3-triazole-4-carboxamide according to claim 1.

16. A method of treating epilepsy comprising administering to subject in need of such treatment a therapeutically effective amount of crystal modification B of the compound 1-(2,6-difluorobenzyl)-1H-1,2,3-triazole-4-carboxamide according to claim 1.

17. A pharmaceutical composition comprising a pharmaceutically acceptable carrier or diluent and a therapeutically effective amount of crystal modification C of the compound 1-(1,6- difluorobenzyl)-1H-1,2,3-trazole-4-carboxamide according to claim 7.

18. A method of treating epilepsy comprising administering to a subject in need of such treatment a therapeutically effective amount of crystal modification C of the compound 1-(2,6-difluorobenzyl)-1H-1,2,3-triazole-4-carboxamide according to claim 7.

* * * * *

UNITED STATES PATENT AND TRADEMARK OFFICE
CERTIFICATE OF CORRECTION

PATENT NO. : 6,455,556 B2
DATED : September 24, 2002
INVENTOR(S) : Portmann et al.

It is certified that error appears in the above-identified patent and that said Letters Patent is hereby corrected as shown below:

Column 8,
Lines 53 and 60, delete "any one of".

Column 9,
Line 36, delete "any one of".

Column 10,
Lines 5 and 11, delete "any one of".

Signed and Sealed this

Eleventh Day of March, 2003

JAMES E. ROGAN
*Director of the United States Patent and Trademark Office*